US00PP27073P3

(12) United States Plant Patent
Ulate

(10) Patent No.: US PP27,073 P3
(45) Date of Patent: Aug. 16, 2016

(54) ***DRACAENA* PLANT NAMED 'EVE'**

(50) Latin Name: *Dracaena fragans*
Varietal Denomination: EVE

(71) Applicant: FLORICA FARMS, INC., Eustis, FL (US)

(72) Inventor: William Vasquez Ulate, Alajuela (CR)

(73) Assignee: Florica Farms, Inc., Eustis, FL (US)

( * ) Notice: Subject to any disclaimer, the term of this patent is extended or adjusted under 35 U.S.C. 154(b) by 30 days.

(21) Appl. No.: 14/544,221

(22) Filed: Dec. 10, 2014

(65) Prior Publication Data

US 2016/0174446 P1 Jun. 16, 2016

(51) Int. Cl.
*A01H 5/00* (2006.01)

(52) U.S. Cl.
USPC ..... Plt./383

(58) Field of Classification Search
USPC ..... Plt./383
CPC ..... A01H 5/00; A01H 5/12
See application file for complete search history.

*Primary Examiner* — Kent L Bell
(74) *Attorney, Agent, or Firm* — Foley & Lardner LLP

(57) ABSTRACT

A new and distinct *Dracaena fragans* plant named 'EVE' particularly characterized by its yellowish to yellowish-green foliage with brilliant yellowish-green margins; long, lanceolate leaves, annual growth rate of about 75 cm, and erect plant habit.

4 Drawing Sheets

Latin name of the genus and species of the claimed plant: *Dracaena fragans*.

Variety denomination: 'EVE'.

BACKGROUND OF THE INVENTION

The present invention relates to a new and distinct cultivar of *Dracaena* plant, botanically known as *Dracaena fragans* var. *massangeana*, of the family Asparagaceae, hereinafter referred to by the cultivar name 'EVE'.

*Dracaena* is a monocotyledonous tropical foliage plant which can be produced as a single or multi-stemmed plant for interior use or outdoors in shade in zones 9 or 10 only.

The new *Dracaena* 'EVE' originated as a naturally-occurring whole plant variation of an unpatented *Dracaena fragans* cultivar 'Massangeana'. The new *Dracaena* 'EVE' was discovered and selected by the inventor William Vásquez Ulate in January 2006, as a single variation within a controlled environment, in Candelaria, Palmares, Alajuela province, Costa Rica.

Asexual reproduction of the new *Dracaena* cultivar by vegetative cuttings was first performed in September 2006 in Candelaria, Palmares, Alajuela, Costa Rica, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'EVE', which in combination distinguish this *Dracaena* as a new and distinct cultivar:

1. Strong yellowish and brilliant yellowish green colored foliage with brilliant yellowish green colored margins and;
2. Long lanceolate leaves;

3. Annual growth rate of about 75 cm; and
4. Erect plant habit.

Plants of the new *Dracaena* 'EVE' differ from plants of the parental cultivar, *Dracaena fragans* 'Massangeana' (unpatented) in the characteristics described in Table 1.

TABLE 1

Comparison with Parent Variety

| Characteristic | New Cultivar 'EVE' | Parent *Dracaena fragans* 'Massangeana' (unpatented) |
|---|---|---|
| Plant Vigor | Less vigorous | More vigorous |
| Color | Strong yellowish and brilliant yellowish green foliage | Deep yellowish and brilliant yellowish green foliage |
| Shape | Lanceolate with curved downwards tips | Lanceolate and wider leaves |
| Texture of leaves | Smooth and waxy | Smooth and waxy |

Of the many commercial cultivars known to the present inventor, the most similar in comparison to the new *Dracaena* 'EVE' is the parent variety, *Dracaena fragans* 'Massangeana', in the characteristics described in Table 1.

BRIEF DESCRIPTION OF THE PHOTOGRAPHS

The accompanying photographs illustrate the overall appearance of the new *Dracaena* cultivar 'EVE' showing the colors as true as is reasonably possible with colored reproductions of this type. Colors in the photographs may differ slightly from the color value cited in the detailed botanical description which accurately describe the color of 'EVE'.

Figure 1:
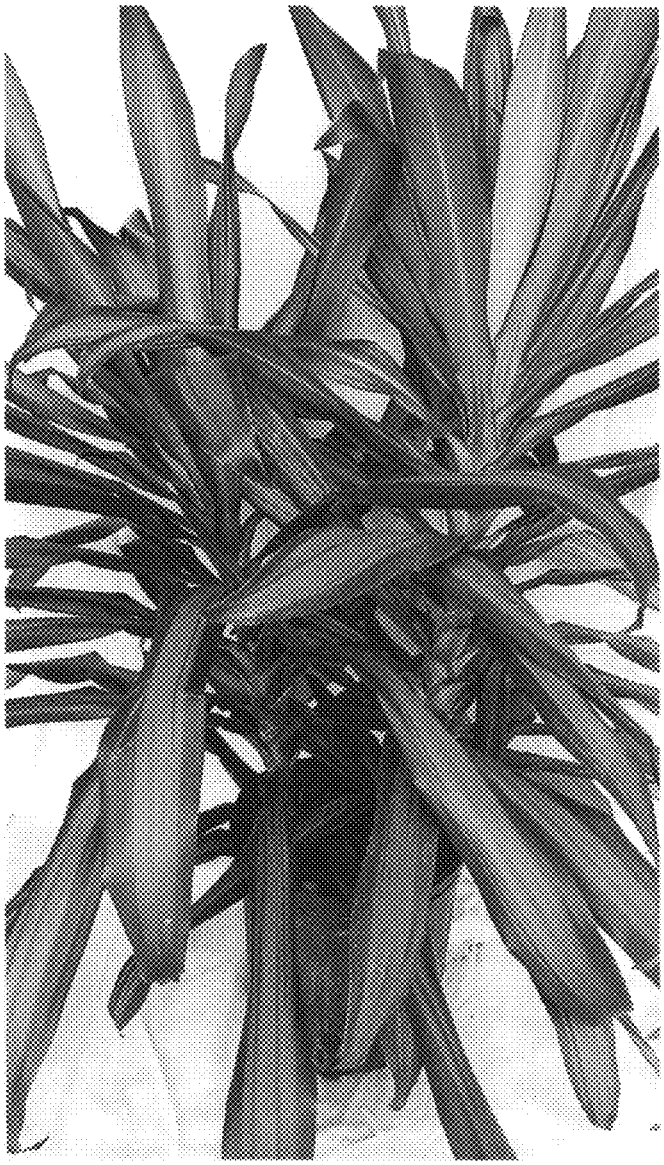

FIG. 1—Side view of a six month old plant of *Dracaena* 'EVE' in a 21 cm diameter pot.

Figure 2:
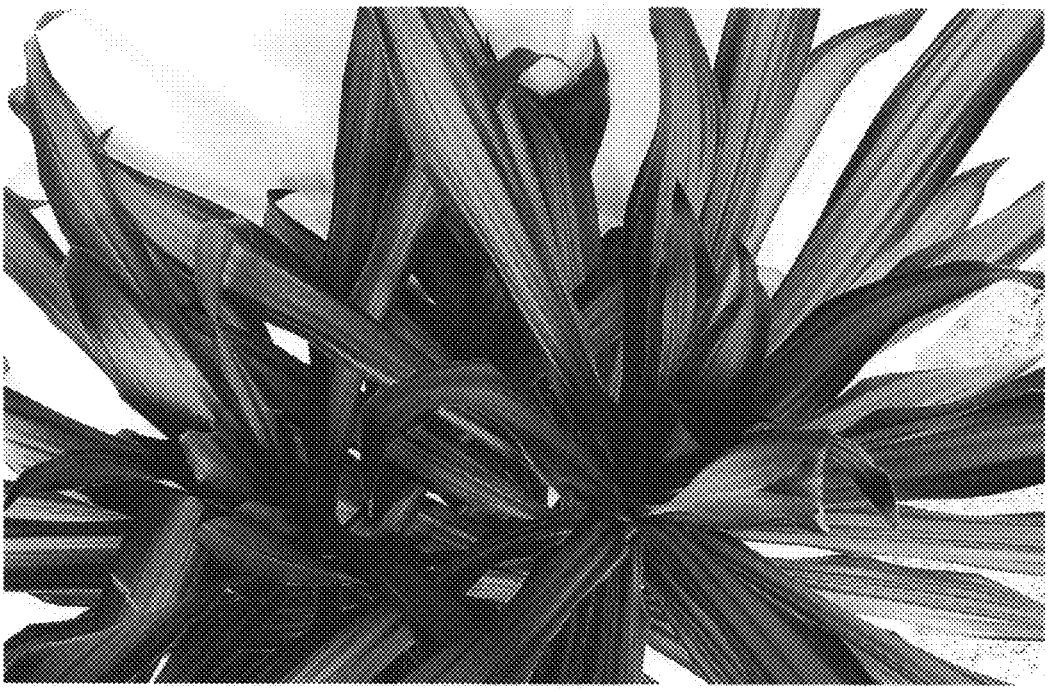

FIG. 2—Top view of a six month old plant of *Dracaena* 'EVE' in a 21 cm diameter pot.

Figure 3:
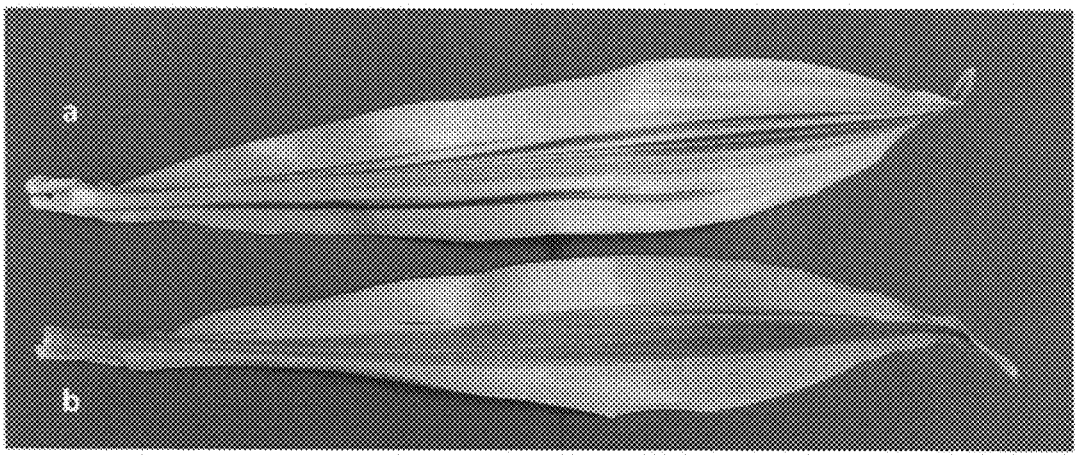

FIGS. 3A and 3B—close-up view of the typical upper surface (A) and lower surface (B) of leaves of 'EVE' at 6 months of age.

Figure 4:
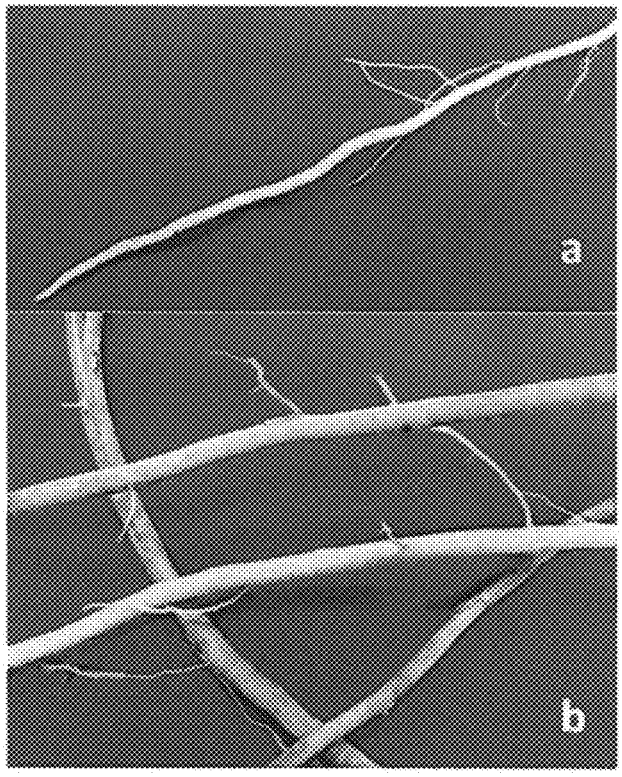

FIGS. 4A and 4B—View of the typical young roots (A) and mature roots (B) of 'EVE' at 6 months of age.

DETAILED BOTANICAL DESCRIPTION

The new *Dracaena* 'EVE' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Dracaena* cultivar 'EVE' as grown in Candelaria, Palmares, Alajuela province, Costa Rica under conditions which closely approximate those generally used in commercial practice. The average temperature is 28° C. during the day and 15° C. at night with natural light conditions. Plants of the new *Dracaena* cultivar 'EVE' are grown under light conditions of about 80% shade from natural sunlight and about 80% relative humidity. No supplementary artificial light is necessary. Plants of the new *Dracaena* 'EVE' are given 1) a liquid 24-8-16 fertilizer weekly, and 2) a granular Nutricote 18-6-12 fertilizer every 100 days. No growth retardants are used when growing plants of the new *Dracaena* 'EVE'.

Color references are made to The Royal Horticultural Society Colour Chart (R.H.S.) The photographs and descriptions were taken during the dry season in Candelaria, Palmares, Alajuela province, Costa Rica in when outdoor day temperatures ranged from 25-28° C. The age of the plants described is 6 months.

Classification:

*Botanical.—Dracaena fragans.*

*Commercial.*—'EVE'.

Parentage: *Dracaena fragans* 'Massangeana' (unpatented).

Optimal growth conditions:

*Light intensity.*—80% shade. Adapts to conditions of light and shade, both interior and exterior.

*Temperature.*—Day: 25° C. to 28° C. Night: 18° C. to 20° C.

*Temperature tolerance.*—Tolerant to a low temperature of about 10° C. and tolerant to a high temperature of about 35° C.

*Fertilization.*—A liquid 24-8-16 fertilizer weekly, and a granular Nutricote 18-6-12 fertilizer every 100 days.

*Growth regulators.*—None.

Propagation:

*Type.*—Vegetative, by air layer or rooted cuttings.

*Rooting habit and description.*—Easy to root. Roots are mostly fibrous and finely branched. In the var. 'EVE', mature plant can present Brilliant Yellow (RHS 7A) roots over 2 m in length and 4-8 mm thick, being thicker at its origin. Young roots are Pale Yellow (RHS 8D) and white towards the tips. The tip is completely white. Young roots tend to produce more secondary roots than mature roots. The secondary roots are 1 mm thick and extend 10 to 12 cm. They can be whitish when they are young and Brilliant Yellow (RHS 7A) when ripe. In the new roots, secondary ones do not achieve more than 6 cm, as the tertiary.

*Time to initiate roots.*—About 10 to 15 days at 25° C.

*Time to produce a rooted cutting.*—About 30 to 45 days at 25° C.

Plant:

*General appearance and form.*—

*Height.*—About 4 m when grown in ground; about 1.5 m when grown in a 21 cm size container.

*Spread.*—About 1 m when grown in ground; About 50 cm when grown in 21 cm size container.

*Form.*—Monocot; leaves whorled, leaf bases wrap around the stem.

*Shape.*—Column.

*Growth rate and habit.*—About 75 cm per year; upright.

*Fragrance.*—None.

*Stem.*—Length: About 4 m when grown in ground; About 1.5 m when grown in 21 cm size container. Diameter: About 40 cm to 50 cm. Shape: round. Texture: rough. Color: RHS 195C Greyed-Green. Strength: very strong. Internode length: About 20 mm to 40 mm.

Foliage:

*Quantity.*—About 25 leaves per stem at 75 cm.

*Arrangement and attachment.*—Single, alternate; leaves whorled; leaf bases wrap around the stem.

*Leaf length.*—About 47 cm.

*Leaf width.*—About 5.5 cm.

*Overall shape of leaf.*—Lanceolate.

*Apex shape.*—Acute, triangular and curved downwards.

*Base shape.*—Plane.

*Margin.*—Sharp, smooth.

*Texture* (*upper and under surface*).—Smooth and waxy.

*Pubescence* (*upper and under surface*).—None.

*Color and dimensions of coloration.*—Upper Surface: Midrib: RHS 143A, Green; about 2 mm wide. Central Band: RHS 144C, Yellow-Green; about 3 cm wide. Longitudinal Stripes: RHS 141C, Green; about 1 to 2 mm wide. Margins: RHS 150C, Yellow-Green; about 1.5 to 2 cm wide. Lower Surface: Midrib: RHS 150D, Yellow-Green; about 4 mm wide. Central Band: RHS 144D, Yellow-Green; about 3.5 cm wide. Margins: RHS 141C, Green; about 1.5 cm wide.

*Venation.*—Pattern: Parallel to the midrib. Color: Upper surface: Green RHS 143A. Lower surface: Yellow-Green RHS150D.

*Leaf fragrance.*—None.

Inflorescence description: No flowering observed.

Reproductive organs: No reproductive organs observed.

Drought tolerance: Moderate.

Disease/pest resistance: None observed.

Disease/pest susceptibility: None observed.

I claim:

1. A new and distinct *Dracaena fragans* plant named 'EVE', substantially as illustrated and described herein.

* * * * *